United States Patent [19]

Solladie et al.

[11] Patent Number: 5,434,281

[45] Date of Patent: Jul. 18, 1995

[54] PROCESS FOR THE STEREOSPECIFIC SYNTHESIS OF LEUKOTRIENE B4 IN ITS 6Z, 8E, 10E CONFIGURATION AND INTERMEDIATES

[75] Inventors: Guy Solladie; Guy Stone, both of Strasbourg, France; Antonio Urbano-Pujol, Madrid, Spain; Jean Maignan, Tremblay les Gonesse, France

[73] Assignee: L'Oreal, Paris, France

[21] Appl. No.: 251,704

[22] Filed: May 31, 1994

[30] Foreign Application Priority Data

Jun. 1, 1993 [FR] France .................... 93 06500

[51] Int. Cl.$^6$ .................. C07C 69/66; C07C 69/73
[52] U.S. Cl. .................... 554/213; 554/127; 554/214; 554/126; 554/150; 554/165; 554/166; 554/196; 554/219; 560/174; 560/177; 560/201; 560/205
[58] Field of Search ............. 554/213, 214, 126, 127, 554/273; 560/174, 177, 201, 205

[56] References Cited

U.S. PATENT DOCUMENTS

| | | | |
|---|---|---|---|
| 4,559,310 | 12/1985 | Cantor et al. | 435/7.21 |
| 4,931,444 | 6/1990 | Van Wauwe et al. | 514/252 |
| 5,185,363 | 2/1993 | Brooks et al. | 514/438 |
| 5,210,208 | 5/1993 | Huang et al. | 548/253 |
| 5,232,948 | 8/1993 | Huang et al. | 514/563 |
| 5,292,907 | 3/1994 | Maignan et al. | 554/127 |
| 5,366,982 | 11/1994 | Dereu et al. | 514/340 |

FOREIGN PATENT DOCUMENTS 0580476 1/1994 European Pat. Off.

OTHER PUBLICATIONS

Lewis et al, "Functional Characterization of Synthetic Leukotriene B and Its Stereochemical Isomers", the Journal of Experimental Medicine, vol. 154, No. 4, 1981, pp. 1243–1248.

*Primary Examiner*—Arthur C. Prescott
*Attorney, Agent, or Firm*—Cushman Darby & Cushman

[57] ABSTRACT

Process for the stereospecific synthesis of leukotriene B4 (LTB4) of 6Z, 8E, 10E configuration of formula

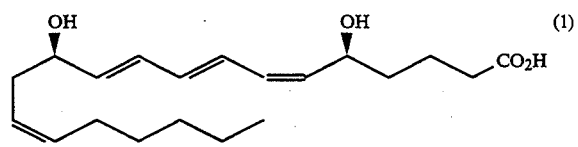

in which a dibenzoate triether is prepared which is subjected to a reductive elimination according to the diagram

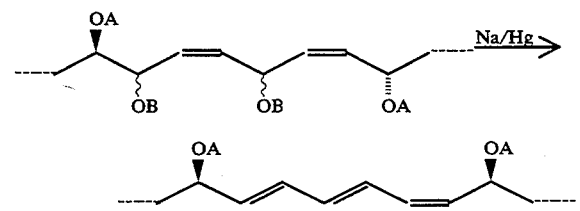

so as to obtain a triether which is converted in order to obtain the leukotriene B4.

29 Claims, 6 Drawing Sheets

PROCESS FOR THE STEREOSPECIFIC SYNTHESIS OF LEUKOTRIENE B4 IN ITS 6Z, 8E, 10E CONFIGURATION AND INTERMEDIATES

The present invention relates to a process for the stereospecific synthesis of leukotriene B4 (hereinafter denoted by LTB4) in its 6Z, 8E, 10E (or 6-cis, 8-trans, 10-trans) configuration and to some intermediates obtained during this process.

It is known that leukotrienes are metabolites of arachidonic acid in leukocytes. Arachidonic acid is converted to an unstable epoxide compound called leukotriene A4, which is itself converted by 5-lipoxygenase to LTB4. LTB4 causes adhesion and chemotactic movement of leukocytes and stimulates aggregation, release of enzymes and the formation of superoxides in neutrophiles. LTB4 is thus implicated in inflammatory and allergic processes.

LTB4 can be isolated with difficulty in sufficient amounts from its biological sources and it is increasingly in demand for pharmacological studies, in particular in the context of biological research on inflammatory processes. In this research, it is extremely important to obtain the leukotriene in a well-determined stereospecific form.

The present invention relates to a process for the stereospecific synthesis of LTB4 in its 6Z, 8E, 10E form, which has the formula:

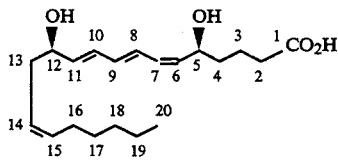

This leucotriene therefore has, in its central triene part, a cis, trans, trans stereochemistry.

Many processes have been proposed for the synthesis of LTB4 having this structure, in particular by Wittig reactions. Such processes are described, for example, in the following documents:

E. J. Corey, A. Marfat, G. Goto, F. Brion, JACS, 1980, 102, 7984; E. J. Corey, A. Marfat, J. Munroe, K. S. Kim, P. B. Mopkius, F. Brion,. Tetrahedron Lett., 1981, 22, 1077; Y. Guindon, R. Zamboni, C. Lau, J. Rokach, Tetrahedron Lett., 1982, 23, 739; R. Zamboni, J. Rokach, Tetrahedron Lett., 1982, 23, 2631; L. J. Mills, P. C. North, Tetrahedron Lett., 1983, 24, 409; K. C. Nicolson, R. E. Zipkin, R. E. Dolle, B. D. Harris, JACS, 1984, 106, 3548; C. K. Hen, D. Di Tullio, Y. F. Wang, C. J. Sih, J. Org. Chem., 1986, 51, 1253; Y. Le Merrer, C. Gravier, D. Languin-Micas, J. C. Depezay, Tetrahedron Lett., 1986, 27, 4161; Y. Kobayashi, T. Shimazaki, F. Seto, Tetrahedron Lett., 1987, 47, 5849; Y. Guindon, D. Delorme, C. K. Len, R. Zamboni, J. Org. Chem., 1988, 53, 267; Y. Le Merrer, C. Granier-Pelletier, D. Micas-Languin, M. Mestre, A. Dureault, J. C. Depezay, J. Org. Chem., 1989, 54, 2409; M. Avignon-Tropis, M. Treilhov, J. Lebreton, J. R. Pougny, I. Frechard-Ortuno, C. Huynh, G. Linstrumelle, Tetrahedron Lett., 1989, 30, 6335; Y. Kobayashi, T. Shimazaki, H. Taguchi, F. Seto, J. Org. Chem., 1990, 55, 5324; M. Avignon-Tropis, M. Treilhov, J. R. Pougny, I. Frechard-Ortuno, G. Linstrumelle, Tetrahedron Lett., 1991, 35, 7279; M. Avignon-Tropis, J. M. Berjeaud, J. R. Pougny, I. Frechard-Ortuno, D. Guillerm, G. Linstrumelle, J. Org. Chem., 1992, 57, 651; M. Treilhov, A. Fauve, J. R. Pougny, J. C. Promé, M. Veschambre, J. Org. Chem., 1992, 57, 3203.

However, these processes do not make it possible to obtain, with a good yield and a good stereospecificity, the LTB4 having the desired cis, trans, trans configuration.

The present invention relates to a process which makes it possible to obtain the desired LTB4 with a better yield and a good stereospecificity.

The subject of the present invention is thus a process for the stereospecific synthesis of LTB4 of 6Z, 8E, 10E configuration having the formula

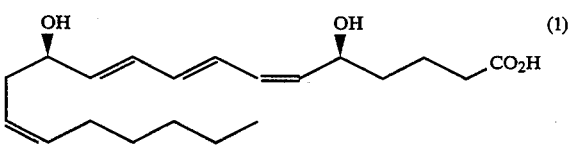

characterized in that:

1) a dibenzoate of formula (2):

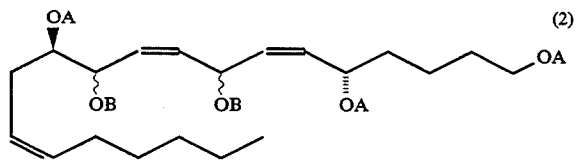

in which formula (2) A represents a silyl radical, in particular tert-butyldimethylsilyl (hereinafter denoted by TBDMS) or tert-butyldiphenylsilyl (hereinafter denoted by TBDPS), it being possible for the three A groups to be silyl radicals which are different from one another, and B represents an unsubstituted benzoyl radical or a benzoyl radical which is substituted by a $C_1$–$C_6$ alkoxy or alkyl radical, preferably an unsubstituted benzoyl radical (hereinafter denoted by Bz), is prepared;

2) the dibenzoate of formula 2) is subjected to a controlled reductive elimination using a sodium amalgam at a temperature between $-10°$ C. and $-30°$ C., in the presence of a solvent, so as to obtain a triether of formula (3):

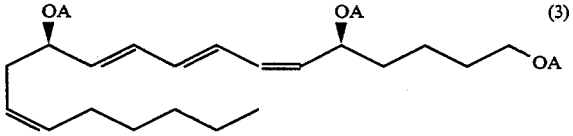

the —OA groups in the 5- and 12-positions of which are then converted to —OH groups and the —CH2OA group in the 1-position of which is then converted to the —COOH group in order to obtain the LTB4 of formula (1).

Tetrahydrofuran or methanol or their mixtures is preferably used as solvent.

In the present description and in the claims, the A and B radicals always correspond to the definitions thereof which have just been provided.

Preferably, in the dibenzoate of formula (2), the alcohol function groups in the 1- and 5-positions are substituted or blocked by tert-butyldimethylsilyl radicals whereas the alcohol in the 12-position is substituted by a tert-butyldiphenylsilyl radical. The B radical is preferably an unsubstituted benzoyl radical (Bz). The preferred compound is thus the dibenzoate of formula (2'):

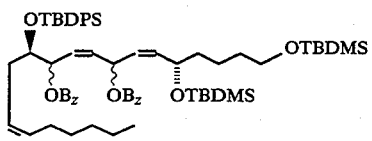

According to the invention, it was thus found that it is possible to form an entirely trans diene from an allylic dibenzoate, while retaining the stereochemistry of the adjacent double bond.

It was known, in the synthesis of vitamin A and of 13-cis retinol (G. Solladié, A. Girardin, G. Lang, J. Org. Chem., 1989, 54, 2620), to carry out the formation reaction of an entirely trans diene from an allylic diol with low valency titanium [Ti(0)]:

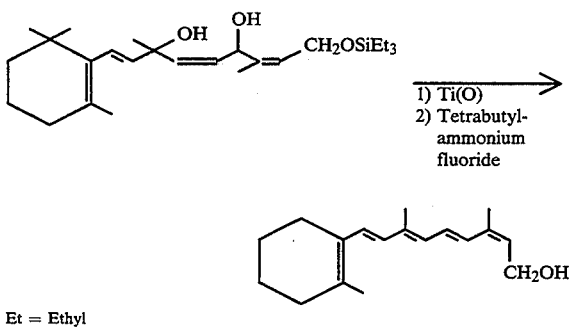

Et = Ethyl

It could therefore be thought that this reaction would be possible when the precursor alcohol of the dibenzoate of formula (2), the central configuration of which is written:

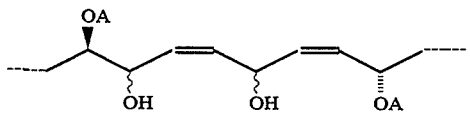

is treated but it turned out that, in the case of the presence of a secondary allylic alcohol on one side and of a secondary bisallylic alcohol on the other, reduction with [Ti(0)] does not give good results. On the other hand, it was found, according to the invention and in an unforeseeable and surprising way, that, by protecting the two alcohols in the dibenzoate form and by using sodium amalgam in place of [Ti(0)] for the monoelectron transfer, the reaction was entirely possible; under excellent conditions, the cis, trans, trans triene yield being quantitative. The reaction can be written diagrammatically in the following way:

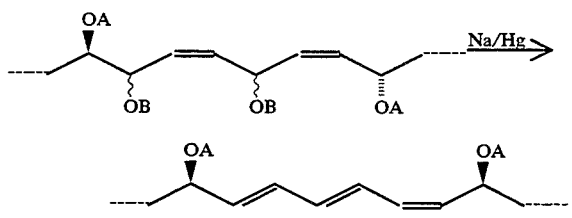

According to the invention, the triene triether of formula (3) is preferably converted to $LTB_4$ of formula (1) in the following way:

1) in a first stage, the triether of formula (3) is reacted with pyridinium dichromate at room temperature in the presence of a solvent, preferably dimethylformamide, so as to obtain the acid of formula (4):

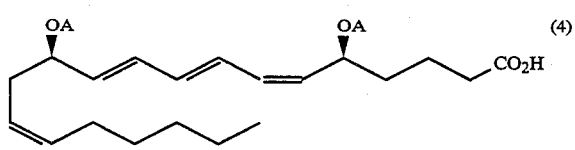

and 2) in a second stage, the acid of formula (4) is treated with a solution of tetrabutylammonium fluoride in a solvent, preferably tetrahydrofuran, in order to obtain the $LTB_4$ of formula (1).

In fact, it was also surprisingly found that it was possible to cleave the silylated ether at the chain end and to oxidize it with pyridinium dichromate without affecting the other two silylated ethers in the 5- and 12-positions.

The dibenzoate of formula (2) is preferably prepared by the following process:

1) in a first stage, a propargyl alcohol of formula (5):

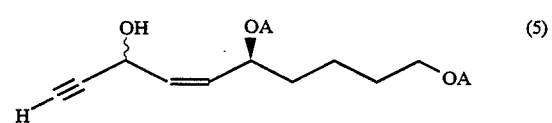

and an aldehyde of formula (6):

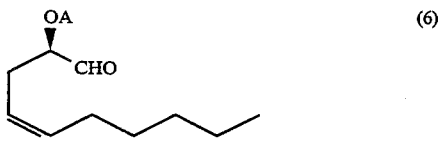

are reacted, the propargyl alcohol of formula (5) being treated beforehand with n-butyllithium, at a temperature between −70° C. and −90° C., in a solvent, preferably tetrahydrofuran, and then reacting with the aldehyde of formula (6) dissolved in a solvent, preferably tetrahydrofuran, the temperature being progressively brought back to room temperature, so as to obtain the propargyl diol of formula (7):

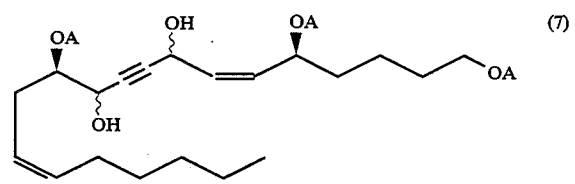

2) in a second stage, the propargyl diol of formula (7), in solution in a solvent, preferably hexane, is reduced with the Lindlar catalyst in the presence of quinoline at room temperature so as to obtain the diol of formula (8):

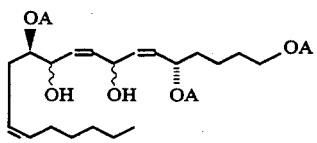 (8)

and 3) in a third stage, the diol of formula (8) is treated with benzoyl chloride in solution in a solvent, preferably pyridine, at room temperature, so as to obtain the dibenzoate of formula (2) defined hereinabove.

The aldehyde of formula (6) defined hereinabove is a known compound which has, for example, been described in G. Solladié, C. Hamdouchi, C. Ziani-Charif, Tetrahedron Asymmetry, 1991, 2, 457.

The Lindlar catalyst consists of Pd/CaCO$_3$/PbO; it is, for example, described in "Fieser and Fieser, Reagents for Organic Synthesis"—J. Wiley, 1967—Vol. 1, page 566.

The propargyl alcohol of formula (5):

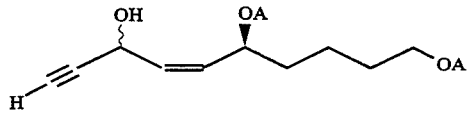 (5)

is preferably prepared by the following process:
1) in a first stage, the aldehyde of formula (9):

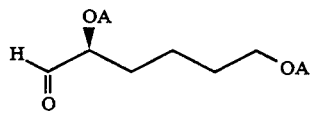 (9)

is used as starting material, this compound having been described, for A=TBDMS, in the 8th stage of the example of French Patent Application 92-08978, filed by the Applicant on 21 Jul. 1992, and it is reacted with triphenylphosphine and zinc powder in a solvent, preferably dichloromethane, and then with CBr$_4$, at room temperature, so as to obtain the dibromide of formula (10):

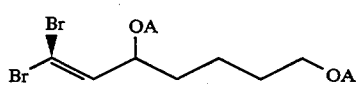 (10)

2) in a second stage, the dibromide of formula (10) is then reacted with n-butyllithium at a temperature of less than −50° C., preferably of the order of −80° C., in a solvent, preferably tetrahydrofuran, in order to obtain the alkyne of formula (11):

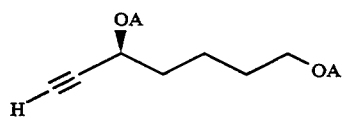 (11)

3) in a third stage, the alkyne of formula (11) in solution in a solvent, preferably tetrahydrofuran, is reacted with an n-butyllithium solution at a temperature of between −70° C. and −90° C. and then with an N-formylpiperidine solution, the temperature being progressively brought back to room temperature, so as to obtain the propargyl aldehyde of formula (12);

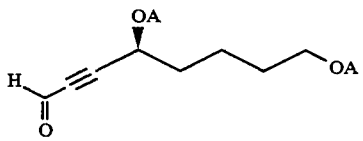 (12)

4) in a fourth stage, the aldehyde of formula (12) is brought together with the Lindlar catalyst and with quinoline in solvent medium, preferably tetrahydrofuran, under a hydrogen atmosphere, so as to obtain the aldehyde of formula (13):

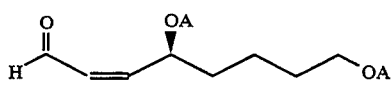 (13)

and 5) in a fifth stage, the aldehyde of formula (13) is dissolved in a solvent, in particular tetrahydrofuran, and then acetylenemagnesium bromide is added so as to obtain the propargyl alcohol of formula (5).

Throughout the present description and in the claims, the term "room temperature" denotes a temperature within the range of those capable of being achieved in an enclosed, non-air-conditioned space in a temperate climate, that is to say a temperature approximately between 5° and 35° C.

Several of the compounds prepared as intermediates during the preparation process defined hereinabove are novel. This is the case with the compounds of formula 2 to 5, 7, 8 and 10 to 13.

Consequently, another subject of the present invention is, as novel chemical compounds useful as intermediates, the following compounds:

a) the dibenzoate of formula

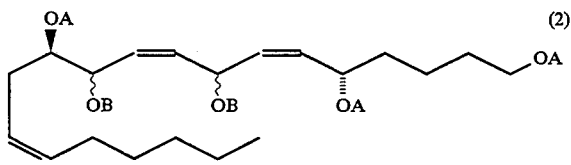 (2)

preferably the dibenzoate of formula

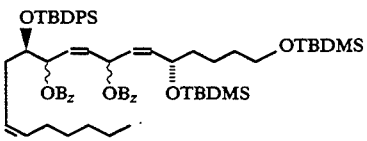 (2')

b) the triene of formula

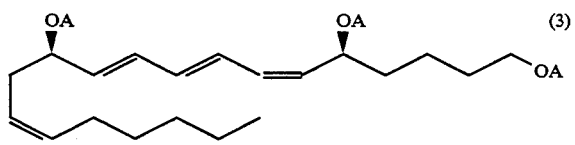 (3)

preferably the triene of formula c) the acid of formula

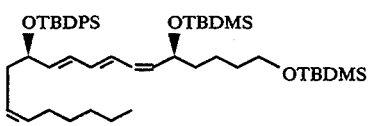

(14)

preferably the acid of formula

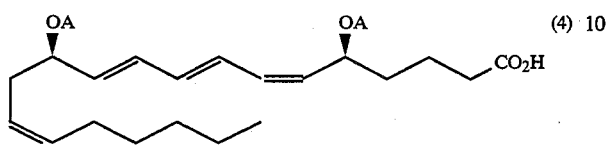

(4)

d) the propargyl alcohol of formula

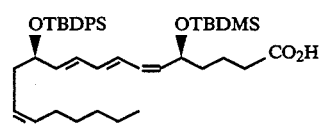

(15)

preferably the propargyl alcohol of formula

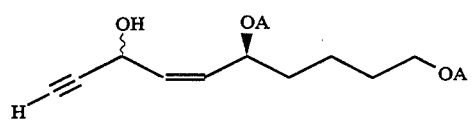

(5)

e) the propargyl diol of formula

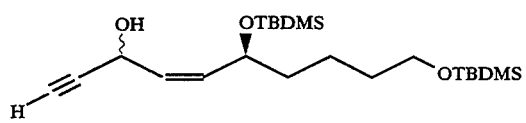

(16)

preferably the propargyl diol of formula

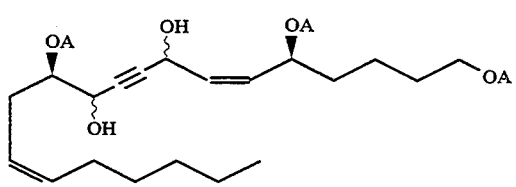

(7)

f) the diol of formula

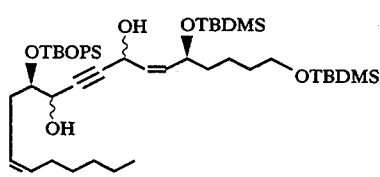

(17)

preferably the diol of formula

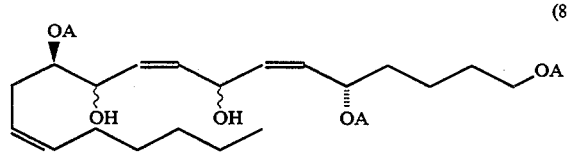

(8)

g) the aldehyde of formula

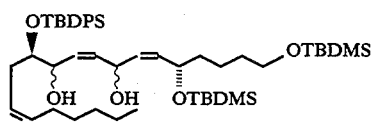

(18)

where at least one of the two A groups represents TBDPS h) the dibromide of formula

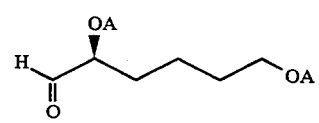

(9)

preferably the dibromide of formula

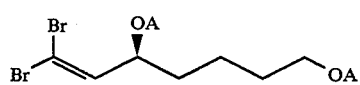

(10)

i) the alkyne of formula

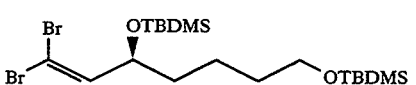

(19)

preferably the alkyne of formula

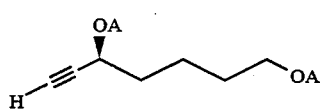

(11)

j) the propargyl aldehyde of formula

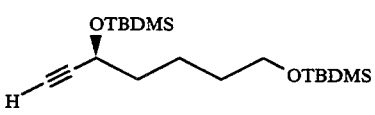

(20)

preferably the propargyl aldehyde of formula

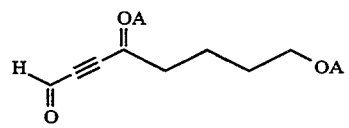

(12)

k) the aldehyde of formula

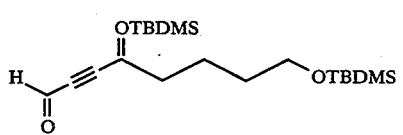

(21)

preferably the aldehyde of formula

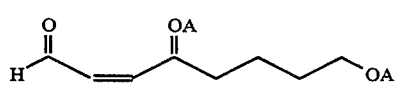

(13)

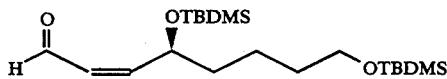

A preparation example is given hereinbelow purely by way of illustration and without implied limitation.

EXAMPLE

Figure 1:
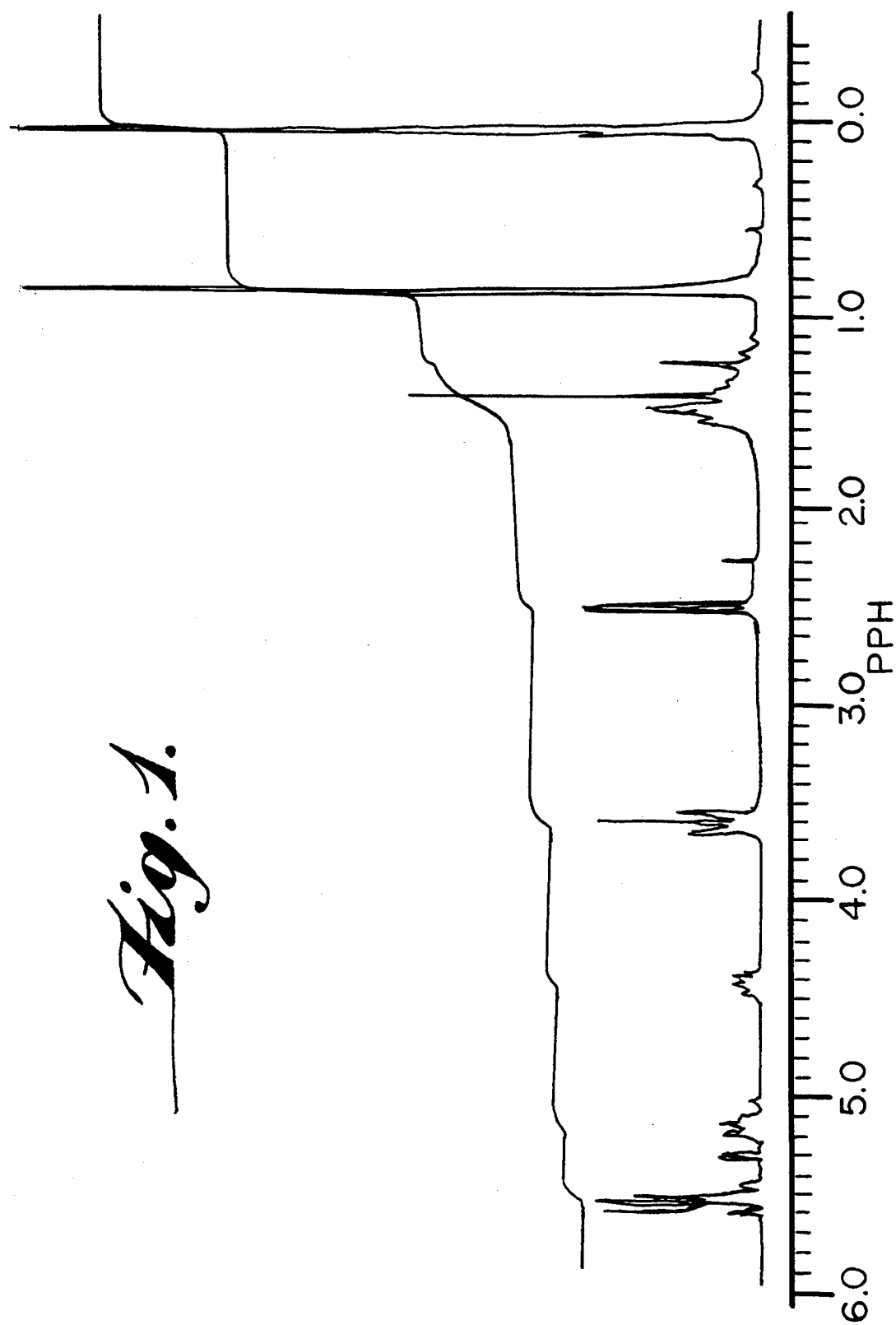
FIGS. 1–6 represent NMR spectrum analysis of compounds of the present invention.

1st Stage: Preparation of (S)-3,7-bis(t-butyldimethylsilyloxy)-1,1-dibromoheptene of Formula

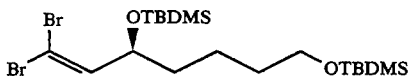

A solution of triphenylphosphine (14.5 g, 55 mmol, 10 equivalents) in $CH_2Cl_2$ (70 ml) is added to zinc powder (3.6 g, 55 mmol, 10 equivalents). A solution of $CBr_4$ (18.25 g, 55 mmol, 10 equivalents) in $CH_2Cl_2$ (80 ml) is then added. The reaction mixture is then stirred for 24 hours at room temperature and (−)-2(S)-2,6-bis(t-butyldimethylsilyloxy)-1-hexanal (2.0 g, 55 mmol) in solution in $CH_2Cl_2$ (50 ml) is added. After stirring for 2 hours, hexane is added and solids are filtered. The solid is washed with hexane and the solvents are evaporated. The crude reaction product is then chromatographed on silica (ether/hexane: 1/100). 2.6 g of pure dibromide (19) (91%) are obtained.

The characteristics of the product obtained are the following:

a) $[\alpha]_D = -2.5°$ (c=1, $CHCl_3$)

b) $^1H$ NMR (200 MHz, $CDCl_3$): δ: 6.37 (d, 1H, J=8.1 Hz, H-2), 4.27 (m, 1H, H-3), 3.61 (t, 2H, J=6.1 Hz, H-7), 1.6–1.3 (m, 6H, H-4, H-5, H-6), 0.89 and 0.88 (2s, 18H, t-Bu), 0.08, 0.06 and 0.05 (3s, 12H, $CH_3$—Si)

c) $^{13}C$ NMR ($CDCl_3$): δ: 142.2 (C-2), 88 (C-1), 73.5 (C-3), 63 (C-7), 36.6 and 32.6 (C-4, C-5), 26 and 25.8 (t-Bu), 21.3 (C-6), 18.4 and 18.1 (C—Si), −4.5, −4.9 and −5.3 ($CH_3$—Si).

2nd Stage: Preparation of the Alkyne of Formula

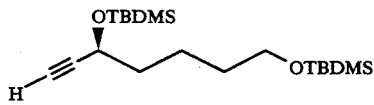

The dibromide (19) (2.6 g, 5 mmol) is dissolved in tetrahydrofuran (THF) (70 ml) and cooled to −78° C. A 1.45M solution of n-butyllithium in hexane (8.6 ml, 12.5 mmol, 2.5 equivalents) is then added dropwise. The reaction mixture is kept stirring for 1 hour at −78° C. and for 1 hour at room temperature. Dilution is carried out with ether and hydrolysis is carried out with a saturated $NH_4Cl$ solution and then washing is carried out with a saturated NaCl solution. After extracting with ether, the product is purified on a silica column (ether/hexane: 1/50) to lead to 1.57 g (88%) of the alkyne (20).

The characteristics of the product obtained are the following:

a) $[\alpha]_D = -27°$ (c=1, $CHCl_3$)

b) $^1H$ NMR (200 MHz, $CDCl_3$): δ: 4.33 (dt, 1H, J=2.1 and 6.2 Hz, H-3), 3.61 (t, 2H, J=6.1 Hz, H-7), 2.36 (d, 1H, J=2.1 Hz, H-1), 1.7–1.4 (m, 6H, H-4, H-5, H-6), 0.90 and 0.89 (2s, 18H, t-Bu), 0.13, 0.10 and 0.04 (3s, 12H, $CH_3Si$), c) $^{13}C$ NMR ($CDCl_3$): 85.6 (C-1), 71.9 (C-2), 63 (C-3), 62.7 (C-7), 38.4 and 32.4 (C-4 and C-5), 26 and 25.7 (t-Bu), 21.6 (C-6), 18.3 and 18.2 (C—Si), −4.57, −5.11 and −5.32 ($CH_3$—Si).

3rd Stage: Preparation of (−)-4(S)-4,8-bis(t-butyldimethylsilyloxy)-2-octyn-1-al of Formula

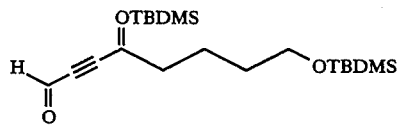

A 1.5M solution of butyllithium in hexane (3 ml, 4.5 mmol, 1.6 equivalents) is added, at −78° C., to the alkyne (20) (1 g, 2.8 mmol) in solution in THF (5 ml). After the addition, the temperature is raised to −40° C. for 1 to 2 hours. A solution of N-formylpiperidine (1 g, 8.8 mmol, 3.1 equivalents) in THF (5 ml) is then added at this temperature. Stirring is continued for one hour at −40° C. and for one hour at room temperature. After diluting with ether, hydrolysis with a saturated $NH_4Cl$ solution, washing of the organic phases with a saturated NaCl solution and evaporation of the solvents, the product is purified by chromatography (ether/hexane: 5/95). 0.9 g (83%) of the aldehyde (21) is obtained.

The characteristics of the product obtained are the following:

a) $[\alpha]_D = -31°$ (c=1, $CHCl_3$)

b) $^1H$ NMR ($CDCl_3$, 200 MHz): δ: 9.22 (s, 1H, H-1), 4.52 (t, 1H, J=6.3 Hz, H-4), 3.61 (t, 2H, J=6.0 Hz, H-8), 1.8–1.4 (m, 6H, H-5, H-6, H-7), 0.90 and 0.88 (2s, 18H, t-Bu), 0.13, 0.11 and 0.04 (3s, 12H, $CH_3Si$), c) $^{13}C$ NMR ($CDCl_3$): δ: 176.1 (C-1), 97.5 and 83.5 (C-2, C-3), 62.6 (C-4, C-8), 37.5 and 32.2 (C-5, C-6), 25.8 and 25.6 (t-Bu), 21.4 (C-7), 18.2 and 18 (C—Si), −4.7, −5.2 and −5.4 ($CH_3$—Si).

4 th Stage: Preparation of (+)-4(S)-4,8-bis(t-butyldimethylsilyloxy)-2(Z)-octen-1-al of Formula

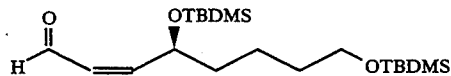

The propargyl aldehyde (21) (700 mg, 1.82 mmol) is dissolved in THF (70 ml). The Lindlar Catalyst (100 mg) and the quinoline (100 μl) are added. Hydrogenation under a hydrogen atmosphere is pursued for one hour. After dilution with ether, filtration through silica and evaporation of the solvents, the product is purified by chromatography (ether/hexane: 5/2). 580 mg (82%) of the aldehyde of formula (22) are isolated.

The characteristics of the product obtained are the following:

a) $[\alpha]_D$: +9° (c=1, $CHCl_3$)

b) $^1H$ NMR: δ: 10.09 (d, 1H, J=7.6 Hz, H-1), 6.48 (dd, 1H, J=8.3 and 11.5 Hz, H-3), 5.89 (ddd, 1H, J=1.1, 7.6 and 11.5 Hz, H-2), 4.95 (m, 1H, H-4), 3.59 (t, 2H, J=6.1 Hz, H-8), 1.7–1.3 (m, 6H, H-5, H-6 and H-7), 0.87 and 0.86 (2s, 18H, t-Bu), 0.05, 0.02 and 0.01 (3s, 12H, CH₃—Si), c) ¹³C NMR (CDCl₃): δ: 191 (C-1), 154.5 and 128 (C-2 and C-3), 68.9 (C-4), 62.8 (C-8), 38 and 32.6 (C-5 and C-6), 25.9 and 25.7 (t-Bu), 21.5 (C-7), 18.3 and 18.1 (C—Si), −4.5, −4.8 and −5.4 (CH₃—Si).

5th Stage: Preparation of 6(S)-6,10-bis(t-butylmethylsilyloxy)-3-hydroxy-4(Z)-decen-1-yne of Formula

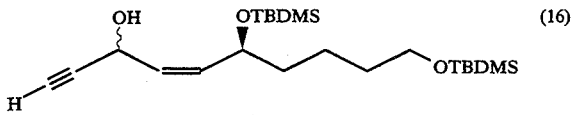
(16)

A 0.5M solution of acetylenemagnesium bromide in THF (6 ml, 3 mmol, 2 equivalents) is added dropwise to the aldehyde (22) (580 mg, 1.5 mmol) in solution in THF (5 ml). After 15 minutes, the reaction mixture is hydrolysed with a saturated NH₄Cl solution, extraction is carried out with ether and the organic phases are washed with a saturated NaCl solution. After evaporation of the solvents and purification by chromatography, 600 mg (97%) of propargyl alcohol (16) (mixture of diastereoisomers) are isolated. FIG. 1 represents the proton NMR spectrum (CDCl₃, 200 MHz). ([α]$_D$=+11° (c=0.65, CHCl₃)).

6th Stage: Preparation of [14(Z), 5(S), 12(R)]-1,5-bis(t-butyldimethylsilyloxy)-14-(t-butyldiphenylsilyloxy)-8,11-bishydroxy-14-eicosen-9-yne of Formula:

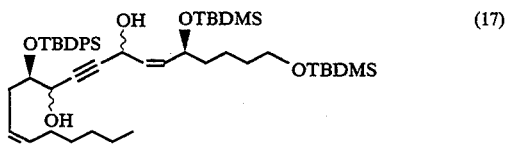
(17)

The propargyl alcohol (16) (600 mg, 1.3mmol, 1 equivalent) in THF (5 ml) is treated with a 1.5M solution of n-butyllithium in hexane (2 ml, 3 mmol, 2.25 equivalents) at −78° C. The temperature is then allowed to rise to −40° C. for 1 to 2 hours and [4(Z), 2(R)]-2-(t-butyldiphenylsilyloxy)-4-decen-1-al of formula:

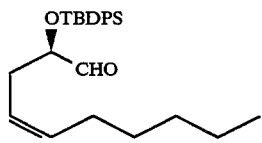

Figure 2:
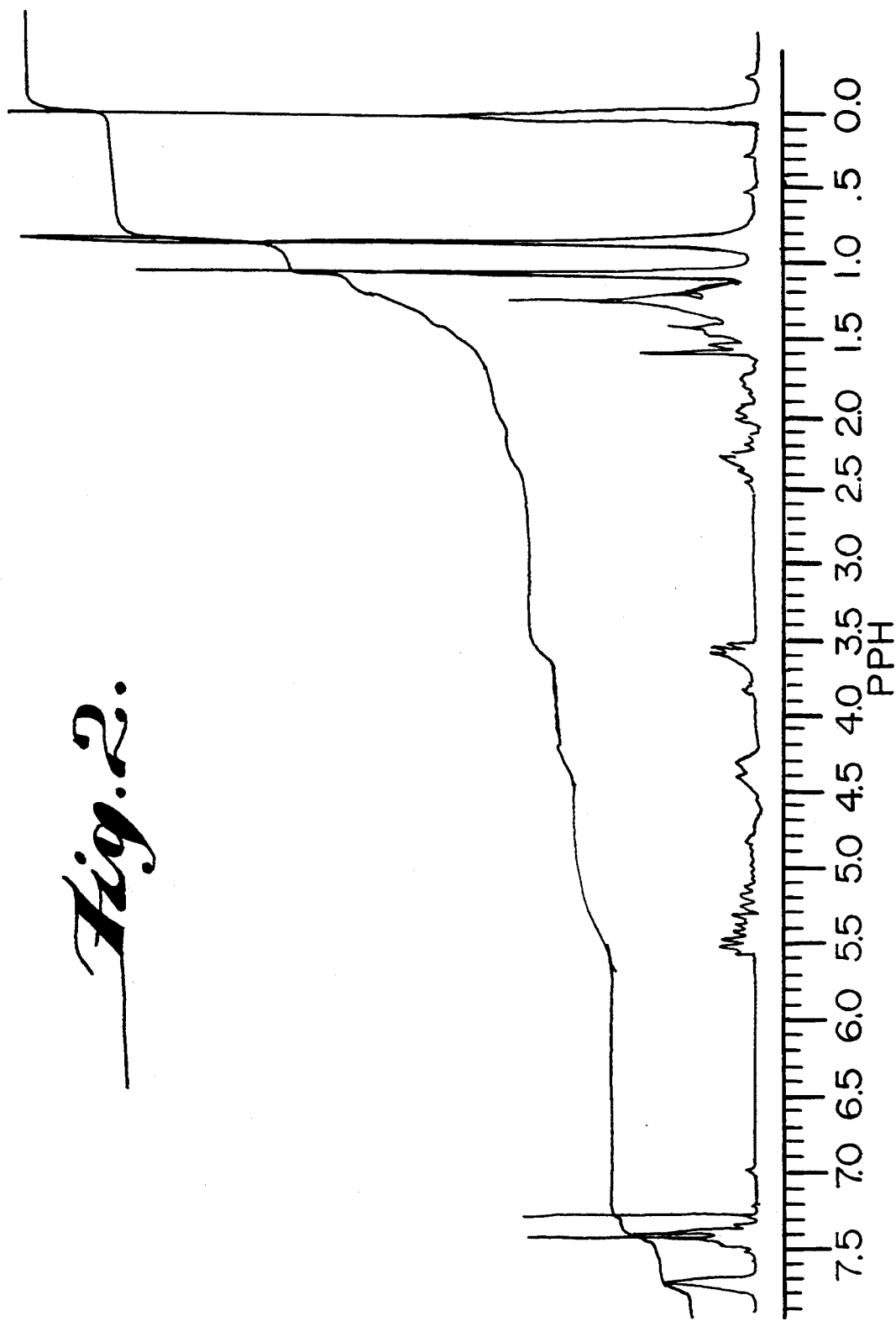

(600 mg, 1.3 mmol, 1 equivalent) in solution in THF (5 ml) is added at this temperature. Stirring is continued at −40° C. for one hour and then at room temperature for one hour. After diluting with ether, hydrolysing with a saturated NH₄Cl solution, washing the organic phases with a saturated NaCl solution, evaporation of the solvents and purification by chromatography (ether/hexane: 30/70), 850 mg (71%) of propargyl diol (17) (mixture of diastereoisomers) are obtained. FIG. 2 represents the proton NMR spectrum (CDCl₃, 200 MHz) ([α]$_D$=+11° (C=2, CHCl₃)).

7th Stage: Preparation of [6(Z), 9(Z), 14(Z), 5(S), 12(R)]-1,5-bis(t-butyldimethylsilyloxy)-12-(t-butyldiphenylsilyloxy)-8,11-dihydroxy-6,9,14-eicosatriene of Formula

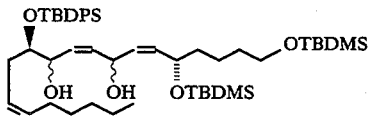
(18)

Figure 3:
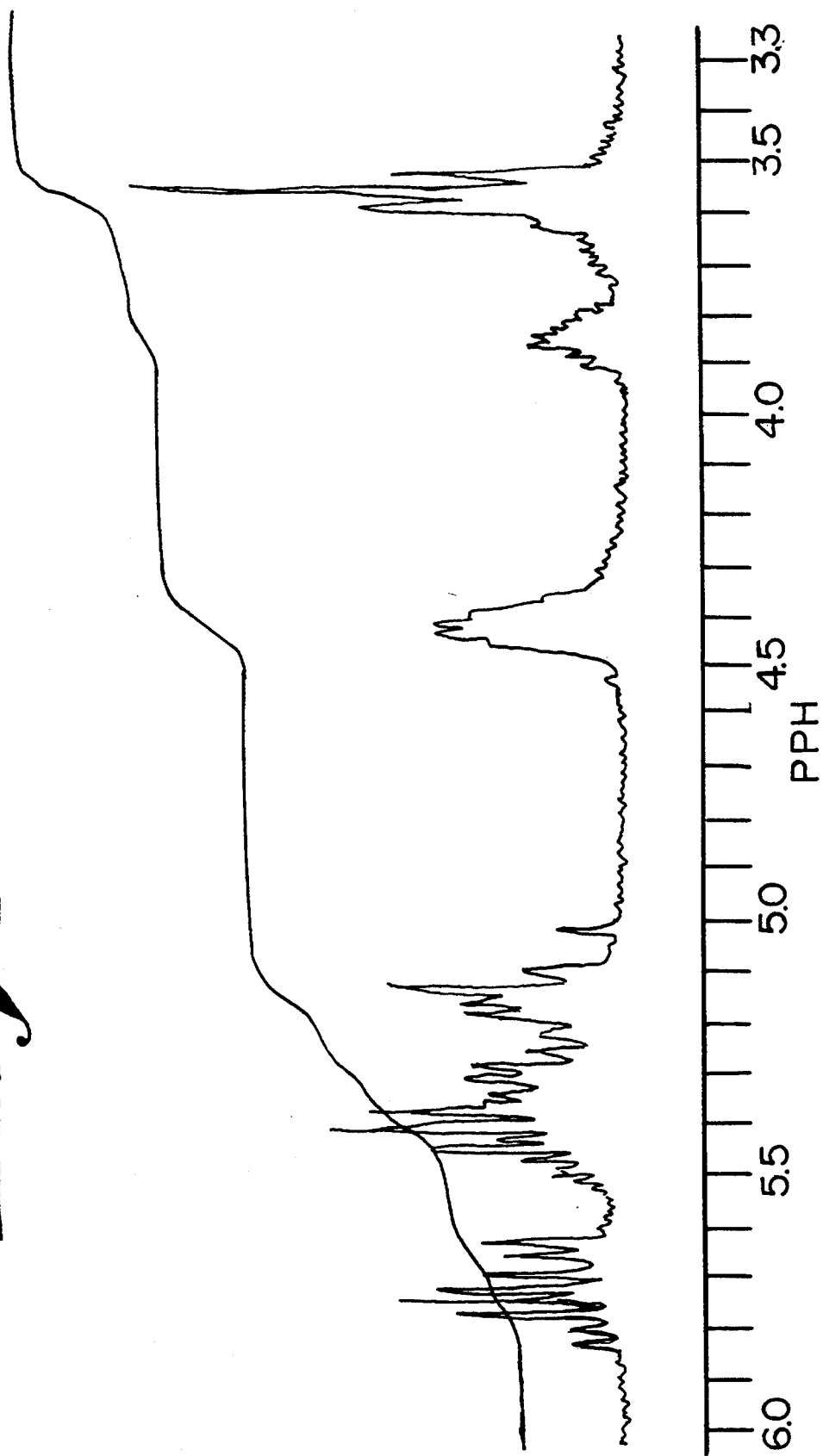
Figure 4:
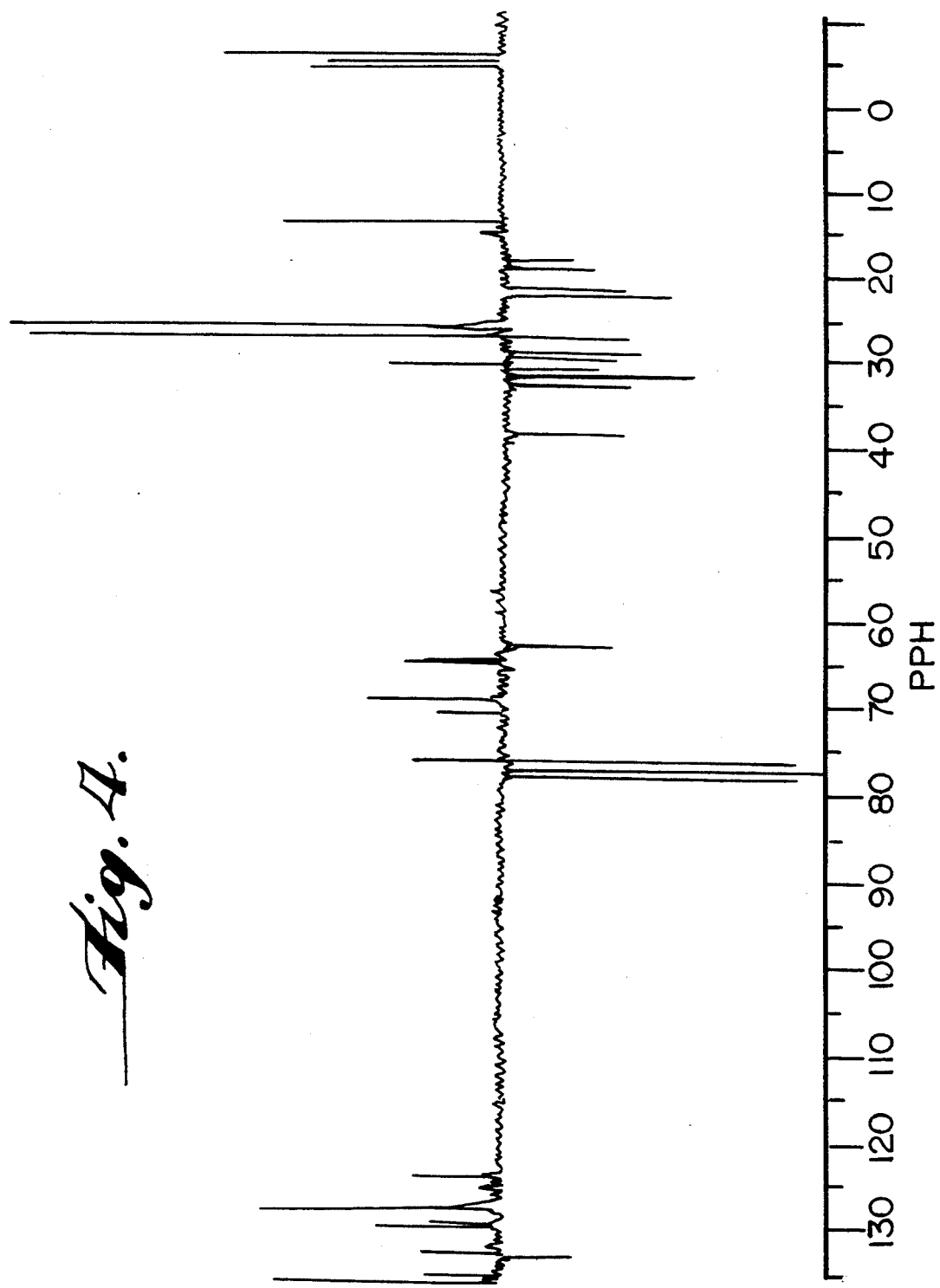

The propargyl diol (17) (400 mg, 0.5 mmol) in solution in hexane (40 ml) is reduced by the Lindlar catalyst (200 mg) in the presence of quinoline (50 ml) under a hydrogen atmosphere for 4 hours. After dilution with ether and filtration through silica gel, the solvents are evaporated and the product purified by chromatography (ether/hexane: 50/50). 225 mg (55%) of diol (18) are obtained in the form of a mixture of diastereoisomers. FIG. 3 represents the proton NMR spectrum (CDCl₃, 200 MHz) and FIG. 4 the ¹³C NMR spectrum (CDCl₃, 200 MHz)

([α]$_D$=+11° (c=2, CHCl₃)).

8th Stage: Preparation of [6Z, 9Z, 14Z, 5(S), 12(R)]-1,5-bis(t-butyldimethylsilyloxy)-12-(t-butyldiphenylsilyloxy)-8,11-bisbenzoxy-6,9,14-eicosatriene of Formula

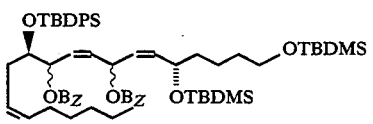
(2')

Figure 5:
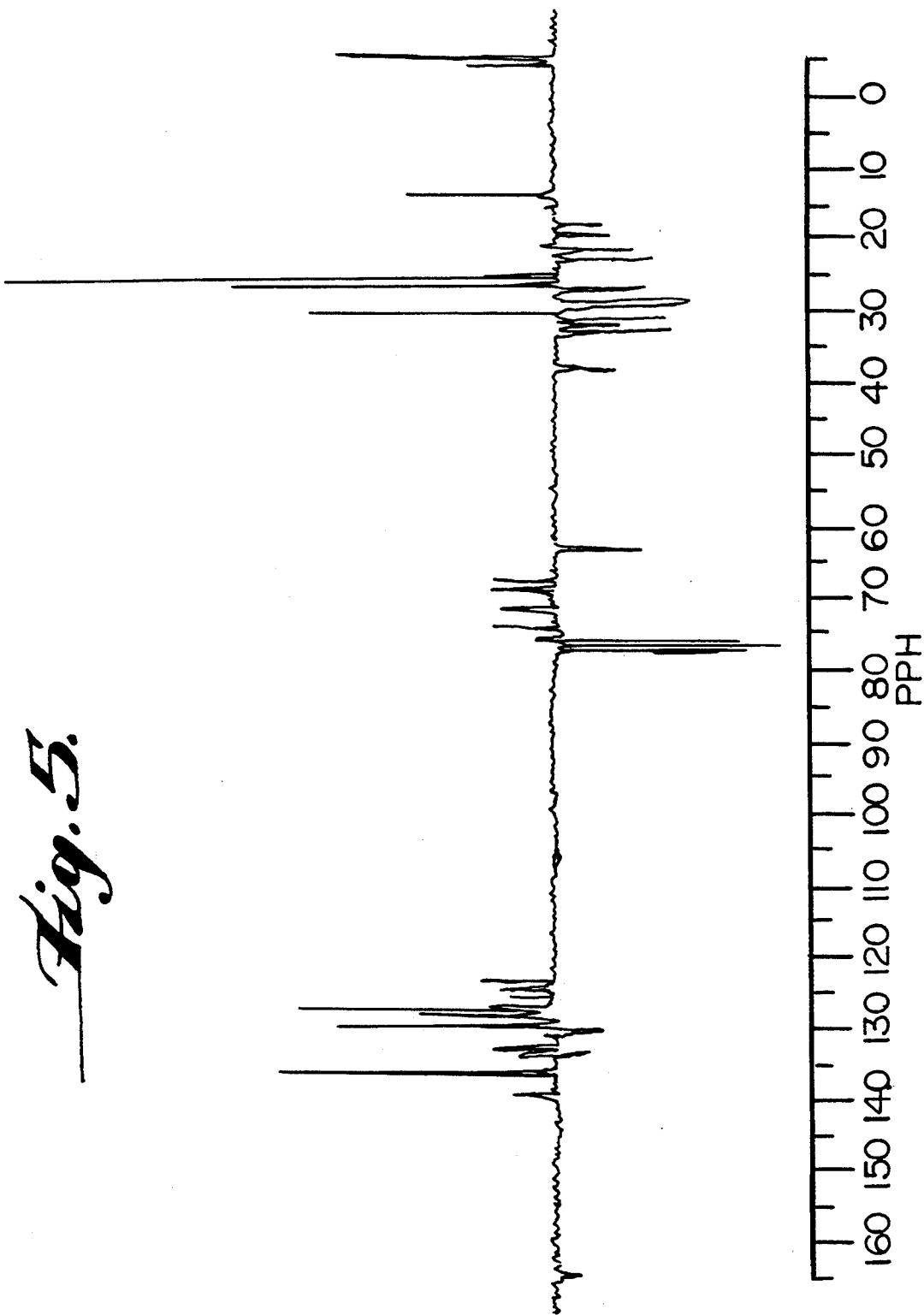
Figure 6:
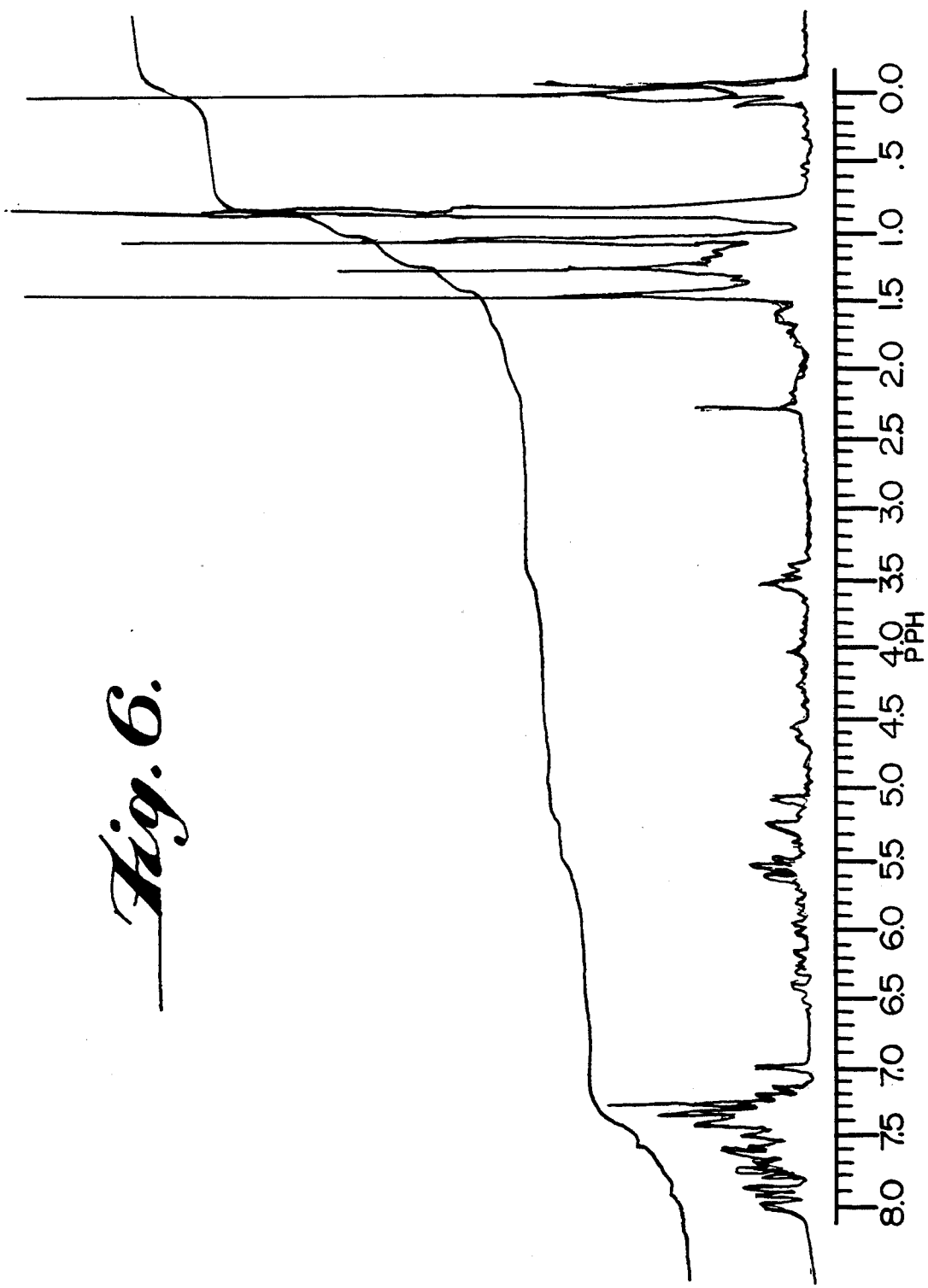

The diol (18) (205 mg, 0.25 equivalent) in solution in pyridine (5 ml) is treated with benzoyl chloride (150 µl, 181.5 mg, 5 equivalents) at 0° C. After stirring for 3 hours at room temperature, dilution is carried out with ether and 5% H₂SO₄ is added. The organic phase is washed with a saturated NH₄Cl and NaCl solution. After evaporation of the solvents and purification by chromatography (ether/hexane: 5/95), 235 mg (90%) of dibenzoate (2') are isolated in the form of a mixture of diastereoisomers. FIG. 5 represents the ¹³C NMR Spectrum obtained. (CDCl₃, 200 MHz) and FIG. 6 the proton NMR spectrum. (CDCl₃, 200 MHz).

9th Stage: Preparation of [6Z, 8E, 10E, 14Z, 5(S), 12(R)]-1,5-bis(t-butyldimethylsilyloxy)-12-(t-butyldiphenylsilyloxy)-6,8,10,14-eicosatetraene of formula:

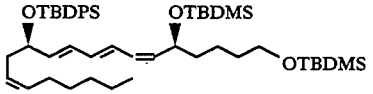
(14)

The dibenzoate (2') (210 mg, 0.2 mmol) in solution in a mixture of THF (10 ml) and methanol (3 ml) is treated with Na₂HPO₄ (200 mg) and, after cooling to −20° C., with 6% by weight sodium amalgam (1 g, 2.6 mmol, 13 equivalents) prepared according to "Reagents for Organic Synthesis, Fieser and Fieser, John Wiley, N.Y., 1967, Vol. 1, page 1030". After reacting for two hours, the reaction mixture is diluted with ether and then filtered through silica gel. After evaporation of the solvents, the product is purified by chromatography. 130 mg (81%) of pure triene (14) are obtained.

The product has the following characteristics:
a) $[\alpha]_D = +48°$ (c=0.3, CHCl$_3$)
b) $^1$H NMR (CDCl$_3$, 200 MHz): δ: 7.71 and 7.39 (2m, 10H, arom. H), 6.29 (dd, 1H, J=11.1 and 14.3 Hz, H-8), 6.08 (m, 1H, H-10), 5.94 (t, 1H, J=10.9 Hz, H-7), 5.92 (dd, 1H, J=10.0 and 15.0 Hz, H-9), 5.69 (dd, 1H, J=6.8 and 14.7 Hz, H-11), 5.5–5.2 (m, 3H, H-6, H-14 and H-15), 4.55 (m, 1H, H-5), 4.22 (q, 1H, J=6.8 Hz, H-12), 3.63 (t, 2H, J=6.1 Hz, H-1), 2.30 (m, 2H, H-16), 1.88 (q, 2H, J=6.4 Hz, H-13), 1.7–1.2 (m, 12H, H-2, H-3, H-4, H-17, H-18, H-19), 1.11 (s, 9H, t-Bu), 0.95–0.85 (m, 21H, t-Bu, H-20), 0.11, 0.08 and 0.07 (3s, 12H, CH$_3$Si), c) $^{13}$C NMR (CDCl$_3$): δ: 136.5, 135.5, 133.4, 132.1, 130.2, 127.5, 127.3 and 124.5 (8 vinyl C), 136 (2C), 135.9 (2C), 134.3, 134.1, 129.5, 129.4, 127.5 (2C) and 127.4 (2C) [10 arom. C], 74 and 69.1 (C-5 and C-12), 63.2 (C-1), 38.3, 36, 32.8, 31.5, 29.2, 27.3, 22.6 and 21.8 (8 aliphat. C), 27.1, 26.0 and 25.9 (9C, t-Bu), 19.3, 18.4 and 18.2 (3C, t-Bu), 14.1 (C-20), −4.2, −4.8 and −5.3 (CH$_3$—Si).

10th Stage: Preparation of 5-(t-butyldimethylsilyloxy)-12-(t-butyldiphenylsilyloxy)-LTB$_4$ of Formula:

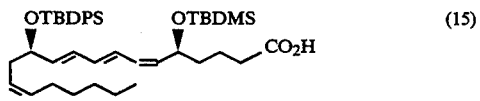

The triene (14) (100 mg, 0.12 mmol) in solution in dimethylformamide is treated with pyridinium dichromate (PDC) (450 mg, 1.2 mmol, 10 equivalents) at room temperature for 24 hours. PDC (225 mg, 0.6 mmol, 5 equivalents) is again added and stirring is again carried out for 24 hours. After dilution with ether, the mixture is treated with a saturated NH$_4$Cl solution. The organic phase is then washed with a saturated NaCl solution. After evaporation of the solvents and preparative thin layer chromatography (silica prewashed with ethanol, eluent: ether/hexane: 30/70, deoxygenated), 53 mg (62%) of the acid (15) are isolated.

The product obtained has the following characteristics:
a) $[\alpha]_D = +65°$ (c=0.6, CHCl$_3$)
b) $^1$H NMR (CDCl$_3$, 200 MHz): δ: 7.65 and 7.35 (2m, 10H, arom. H), 6.25 (dd, 1H, J=11.0 and 14.3 Hz, H-8), 6.06 (m, 1H, H-10), 5.33 (t, 1H, J=11.0 Hz, H-7), 5.91 (dd, 1H, J=9.8 and 15.0 Hz, H-9), 5.66 (dd, 1H, J=6.7 and 14.7 Hz, H-11), 5.5–5.2 (m, 3H, H-6, H-14, H-15), 4.53 (m, 1H, H-5), 4.20 (q, 1H, J=6.7 Hz, H-12), 2.4–2.1 (m, 4H, H-2, H-16), 1.85 (m, 2H, H-13), 1.7–1.2 (m, 10H, H-3, H-4, H-17, H-18, H-19), 1.08 (s, 9H, t-Bu), 0.9–0.8 (m, 12H, t-Bu and H-20), 0.08 and 0.04 (2s, CH$_3$—Si), c) $^{13}$C NMR (CDCl$_3$): δ: 179.4 (C-1), 136.8, 134.8, 134.7, 132.1, 130.1, 127.9, 127.0 and 124.5 (8 vinyl C), 136.0 (2C), 135.9 (2C), 134.3, 134.1, 129.5, 129.4, 127.5 (2C) and 127.4 (2C) [12 arom. C], 73.9 and 68.6 (C-5, C-12), 37.7, 36.0, 33.9, 31.5, 29.2, 27.3, 22.6 and 20.6 (8 aliphat. C), 27.0 and 25.9 (6C, t-Bu), 19.3 and 18.1 (2C, t-Bu), 14.1 (C-20), −4.2 and −4.8 (CH$_3$—Si).

11th Stage: Preparation of the LTB$_4$ of Formula:

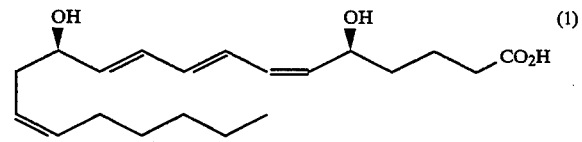

Hydrolysis of the silylated ethers of the acid (15) was carried out under the conditions described by Kobayashi et al., J. Org. Chem., 1990, 55, 5324. A 1.1M solution of tetrabutylammonium fluoride (TBAF) in THF (650 μl, 0.7 mmol) is added to the acid (15) (50 mg, 0.07 mmol) dissolved in THF (2 ml). After 24 hours at room temperature, dilution is carried out with ether and hydrolysis is carried out with a phosphate buffer (prepared from 7.38 g of Na$_2$HPO$_4$.12H$_2$O and 2.04 g of citric acid in 200 ml of water). The organic phase is washed with a saturated NaCl solution, the solvents are evaporated and purification is carried out by chromatography on a preparative silica plate (prewashed with ethanol, eluent: methanol/ether: 2/98, deoxygenated) in order to obtain 16.7 mg (71%) of LTB$_4$.

The LTB$_4$ obtained has the following characteristics:
a) $[\alpha]_D = +12.7°$ (c=0.3, CDCl$_3$)
b) $^1$H NMR (CDCl$_3$, 200 MHz): δ: 6.49 (dd, 1H, H=11.7 Hz and 14.0 Hz, H-8), 6.27 (m, 2H, H-9 and H-10), 6.08 (t, 1H, J=11.0 Hz, H-7), 5.78 (dd, 1H, J=6.2 and 14.4 Hz, H-11), 5.65–5.30 (m, 3H, H-6, H-14 and H-15), 4,60 (m, 1H, H-5), 4.22 (q, 1H, J=6.4 Hz, H-12), 2.5–2.2 (m, 4H, H-2 and H-13), 2.15–1.95 (m, 2H, H-16), 1.8–1.2 (m, 12H, H-3, H-4, H-17, H-18,=H-19, H-20), 0.88 (t, 3H, J=6.5 Hz, H-20), c) $^{13}$C NMR (CDCl$_3$): 178.9 (C-1), 137.1, 134.8, 134.1, 132.9, 130.4, 127.7, 127.0, 124.4 (8 vinyl C), 72.9 and 68.1 (C-5 and C-12), 36.9, 35.6, 33.9, 31.5, 29.2, 27.3, 22.6, 20.5 (8 aliphat. C), 14.1 (C-20).

The NMR spectrum of the LTB$_4$ obtained corresponds to that described in the literature for this compound.

We claim:
1. Process for the stereospecific synthesis of leukotriene B$_4$ (LTB$_4$) of 6Z, 8E, 10E configuration having the formula

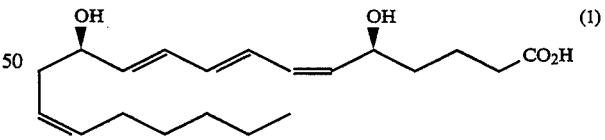

characterized in that:
1) a dibenzoate of the formula (2)

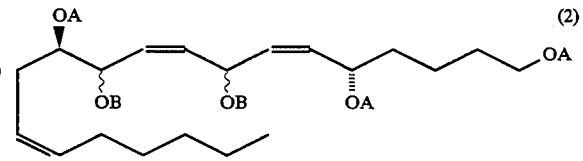

in which formula (2) A represents a silyl group and B represents an unsubstituted benzoyl radical or a benzoyl radical substituted by a C$_1$–C$_6$ alkoxy or alkyl radical, is prepared;

2) the dibenzoate of formula (2) is subjected to a controlled reductive elimination using a sodium amalgam at a temperature between −10° C. and −30° C., in the presence of a solvent, so as to obtain a triether of formula (3):

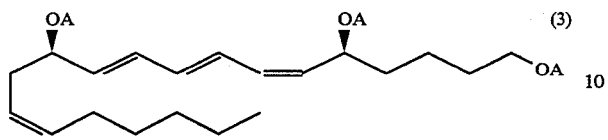

the —OA groups in the 5- and 12-positions of which are then converted to —OH groups and the —CH₂OA group in the 1-position of which is then converted to the —COOH group in order to obtain the leukotriene B₄ of formula (1).

2. Process according to claim 1, characterized in that, in the formula (2), A represents a silyl group chosen from the group formed by tert-butyldimethylsilyl (TBDMS) and tert-butyldiphenylsilyl (TBDPS), it being possible for the A groups to be different from one another.

3. Process according to claim 2, characterized in that the dibenzoate of formula (2) has the formula

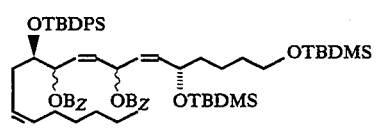

Bz being an unsubstituted benzoyl radical.

4. Process according to claim 1, characterized in that the reductive elimination is carried out using a sodium amalgam in the presence of a solvent chosen from the group formed by tetrahydrofuran or methanol or their mixtures.

5. Process according to claim 1, characterized in that the triether of formula (3) is converted to leukotriene B₄ of formula (1) by the following stages:
1) in a first stage, the triether of formula (3) is reacted with pyridinium dichromate at room temperature in the presence of a solvent so as to obtain the acid of formula (4):

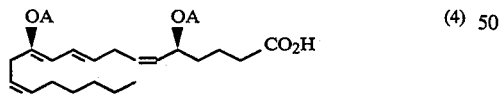

and
2) in a second stage, the acid of formula (4) is treated with a solution of tetrabutylammonium fluoride in a solvent in order to obtain the leukotriene B₄ of formula (1).

6. Process according to claim 5, characterized in that dimethylformamide is used as solvent in the first stage and tetrahydrofuran is used as solvent in the second stage.

7. Process according to claim 1, characterized in that the dibenzoate of formula (2) is prepared by the following stages:
1) in a first stage, a propargyl alcohol of formula (5):

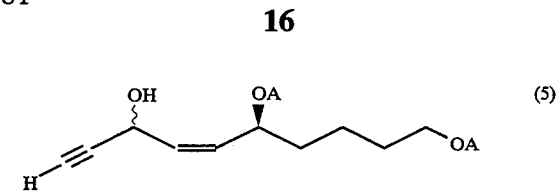

and an aldehyde of formula (6):

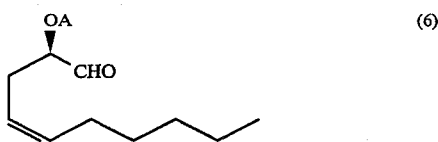

are reacted, the propargyl alcohol of formula (5) being treated beforehand with n-butyllithium, at a temperature between −70° C. and −90° C., in a solvent, and then reacting with the aldehyde of formula (6) dissolved in a solvent, the temperature being progressively brought back to room temperature, so as to obtain the propargyl diol of formula (7):

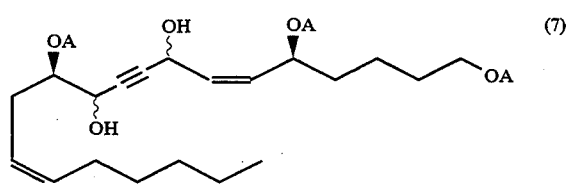

2) in a second stage, the propargyl diol of formula (7), in solution in a solvent, is reduced with the Lindlar catalyst in the presence of quinoline at room temperature, so as to obtain the diol of formula (8):

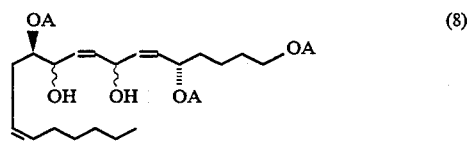

and
3) in a third stage, the diol of formula (8) is treated with benzoyl chloride in solution in a solvent, at room temperature, so as to obtain the dibenzoate of formula (2).

8. Process according to claim 7, characterized in that tetrahydrofuran is used as solvent in the first stage and hexane is used as solvent in the second stage.

9. Process according to claim 7, characterized in that the propargyl alcohol of formula (5):

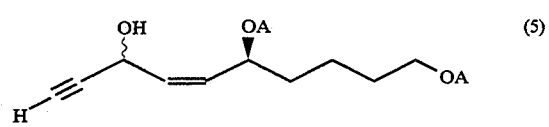

is prepared by the following stages:
1) in a first stage, the aldehyde of formula (9):

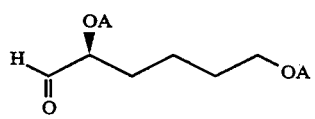 (9)

is used as starting material, and it is reacted with triphenylphosphine and zinc powder in a solvent and then with CBr$_4$, at room temperature, so as to obtain the dibromide of formula (10):

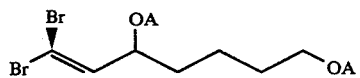 (10)

2) in a second stage, the dibromide of formula (10) is then reacted with n-butyllithium at a temperature of less than −50° C. in a solvent in order to obtain the alkyne of formula (11):

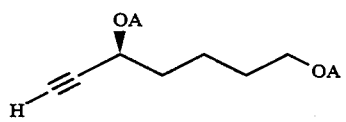 (11)

3) in a third stage, the alkyne of formula (11) in solution in a solvent is reacted with an n-butyllithium solution at a temperature of between −70° C. and −90° C. and then with an N-formylpiperidine solution, the temperature being progressively brought back to room temperature, so as to obtain the propargyl aldehyde of formula (12);

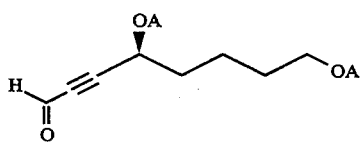 (12)

4) in a fourth stage, the aldehyde of formula (12) is brought together with the Lindlar catalyst and with quinoline in solvent medium under a hydrogen atmosphere, so as to obtain the aldehyde of formula (13):

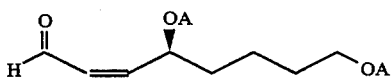 (13)

and 5) in a fifth stage, the aldehyde of formula (13) is dissolved in a solvent and then acetylenemagnesium bromide is added so as to obtain the propargyl alcohol of formula (5).

10. Process according to claim 9, characterized in that:
in the first stage, dichloromethane is used as solvent;
in the second stage, the reaction is carried out at a temperature of the order of −80° C. in tetrahydrofuran;
in the third stage, the alkyne of formula (11) is reacted in solution in tetrahydrofuran;
in the fourth stage, tetrahydrofuran is used as solvent, and
in the fifth stage, the aldehyde of formula (13) is dissolved in tetrahydrofuran.

11. Dibenzoate of formula

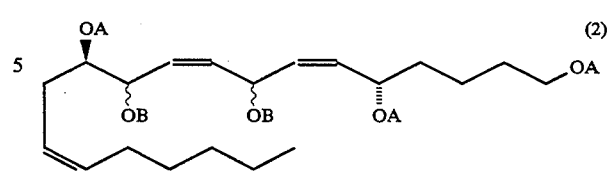 (2)

in which formula A represents, independently of one another, a tert-butyldimethylsilyl (TBDMS) group or a tert-butyldiphenylsilyl (TBDPS) group and B represents an unsubstituted benzoyl radical (Bz) or a benzoyl radical substituted by a $C_1$-$C_6$ alkoxy or alkyl radical.

12. Dibenzoate according to claim 11, of formula

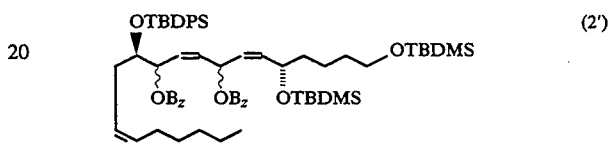 (2')

where TBDMS, TBDPS and Bz have the meaning given in claim 11.

13. Triene of formula

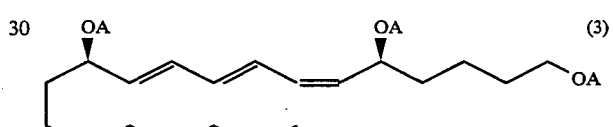 (3)

where A has the same meaning as in claim 11.

14. Triene of formula

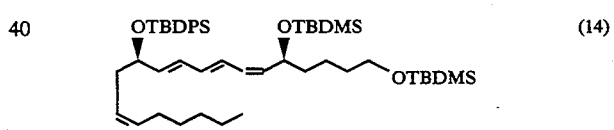 (14)

where TBDMS and TBDPS have the same meaning as in claim 11.

15. Acid of formula

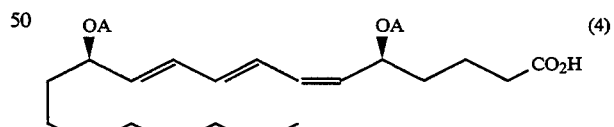 (4)

where A has the same meaning as in claim 11.

16. Acid of formula

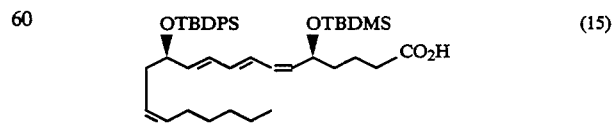 (15)

where TBDMS and TBDPS have the same meaning as in claim 11.

17. Propargyl alcohol of formula

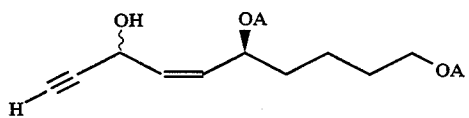 (5)

where A has the same meaning as in claim 11.
18. Propargyl alcohol of formula

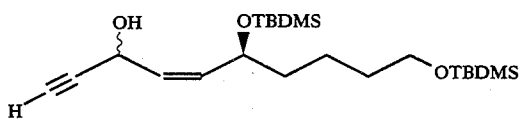 (16)

where TBDMS has the same meaning as in claim 11.
19. Propargyl diol of formula

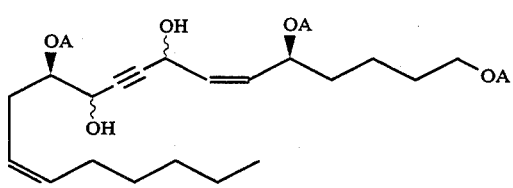 (7)

where A has the same meaning as in claim 11.
20. Propargyl diol of formula

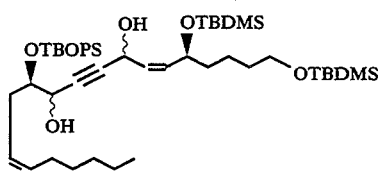 (17)

where TBDMS and TBDPS have the same meaning as in claim 11.
21. Dibromide of formula

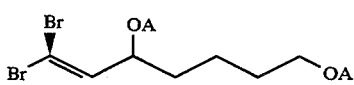 (10)

where A has the same meaning as in claim 11.
22. Dibromide of formula

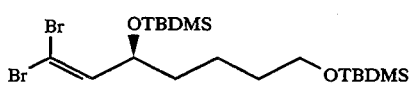 (19)

where TBDMS has the same meaning as in claim 11.
23. Alkyne of formula

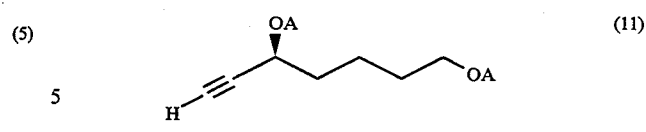 (11)

where A has the same meaning as in claim 11.
24. Alkyne of formula

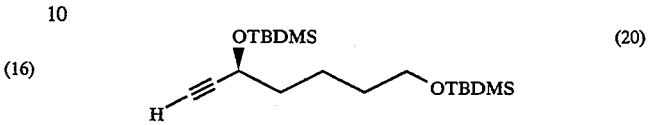 (20)

where TBDMS has the same meaning as in claim 11.
25. Propargyl aldehyde of formula

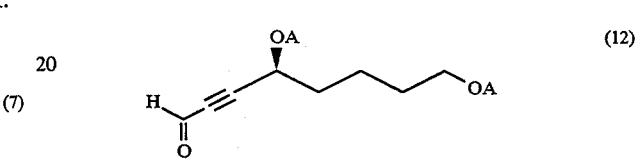 (12)

where A has the same meaning as in claim 11.
26. Propargyl aldehyde of formula

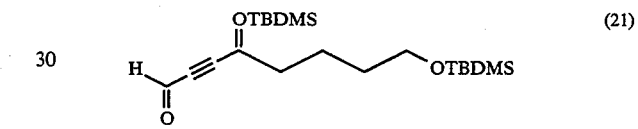 (21)

where TBDMS has the same meaning as in claim 11.
27. Aldehyde of formula

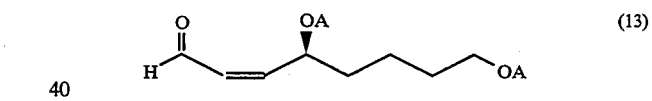 (13)

where A has the same meaning as in claim 11.
28. Aldehyde of formula

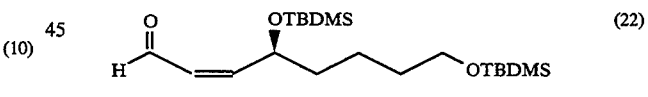 (22)

where TBDMS has the same meaning as in claim 11.
29. Aldehyde of formula

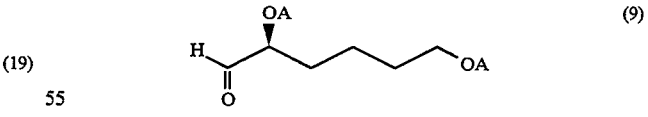 (9)

where at least one of the two A groups represents TBDPS, TBDPS having the meaning given in claim 11.

* * * * *